US008801788B2

(12) United States Patent
Merves

(10) Patent No.: US 8,801,788 B2
(45) Date of Patent: Aug. 12, 2014

(54) EXPANDABLE MEDICAL IMPLANT

(71) Applicant: Michael Merves, Memphis, TN (US)

(72) Inventor: Michael Merves, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/897,880

(22) Filed: May 20, 2013

(65) Prior Publication Data

US 2013/0253653 A1 Sep. 26, 2013

Related U.S. Application Data

(62) Division of application No. 13/015,231, filed on Jan. 27, 2011.

(51) Int. Cl.
*A61F 2/44* (2006.01)
*A61B 17/88* (2006.01)

(52) U.S. Cl.
USPC .......................................... 623/17.11; 606/279

(58) Field of Classification Search
CPC ............. A61B 2017/0256; A61F 2002/30235; A61F 2002/3055; A61F 2002/3061; A61F 2/46; A61F 2/4455; A61F 2/446; A61F 2/4611
USPC ............................ 623/17.11–17.16; 606/279
See application file for complete search history.

(56) References Cited

U.S. PATENT DOCUMENTS 1,486,723 A 7/1921 Bernson
4,401,112 A 8/1983 Rezaian
4,553,273 A 11/1985 Wu
4,554,914 A 11/1985 Kapp
4,657,550 A 4/1987 Daher
5,236,460 A 8/1993 Barber
5,360,430 A 11/1994 Lin
5,443,515 A 8/1995 Cohen et al.
5,480,442 A 1/1996 Bertagnoli
5,571,192 A 11/1996 Schonhoffer
5,702,453 A 12/1997 Rabbe et al.
5,702,455 A 12/1997 Saggar
5,723,013 A 3/1998 Jeanson et al.
5,725,528 A 3/1998 Errico et al.
5,776,197 A 7/1998 Rabbe
5,776,198 A 7/1998 Rabbe
5,827,328 A 10/1998 Buttermann
5,865,848 A 2/1999 Baker
5,916,267 A 6/1999 Tienboon
5,989,290 A 11/1999 Biedermann et al.
6,015,436 A 1/2000 Schonhiffer
6,156,038 A 12/2000 Zucherman
6,159,244 A 12/2000 Suddaby
6,174,334 B1 1/2001 Suddaby
6,176,881 B1 1/2001 Schar et al.
6,190,413 B1 2/2001 Sutcliffe
6,190,414 B1 2/2001 Young et al.

(Continued)

*Primary Examiner* — Ellen C Hammond
*Assistant Examiner* — Jacqueline Johanas

(57) ABSTRACT

An implant with an adjustable height for spacing apart skeletal structures. The implant includes a base with a hollow interior. Collars include threaded inner surfaces and are positioned within the hollow interior of the base and are rotatable relative to the base. Threaded posts extend outward from the base and are threaded into the collars. Rotation of the collars adjusts an amount that the threaded posts extend outward from the base. An overall height of the implant can be adjusted to accommodate the size of the space and for the posts to contact against and space apart the skeletal structures.

17 Claims, 12 Drawing Sheets

200
10
40
201
20
36
30
78
25
77
79
30
36
40
200

(56) References Cited

U.S. PATENT DOCUMENTS 6,200,348 B1 3/2001 Biedermann et al.
6,296,665 B1 10/2001 Strnad et al.
6,299,642 B1 10/2001 Chan
6,299,644 B1 10/2001 Vanderschot
6,332,895 B1 12/2001 Suddaby
6,344,057 B1 2/2002 Rabbe et al.
6,375,683 B1 4/2002 Crozet et al.
6,395,034 B1 5/2002 Suddaby
6,409,766 B1 6/2002 Brett
6,436,142 B1 8/2002 Paes et al.
6,447,547 B1 9/2002 Michaelson
6,454,806 B1 9/2002 Cohen et al.
6,520,991 B2 2/2003 Huene
6,524,341 B2 2/2003 Lang et al.
6,562,074 B2 5/2003 Gerbec et al.
6,610,090 B1 8/2003 Bohm et al.
6,616,695 B1 9/2003 Crozet et al.
6,645,249 B2 11/2003 Ralph
6,648,917 B2 11/2003 Gerbec et al.
6,652,584 B2 11/2003 Michaelson
6,660,038 B2 12/2003 Boyer, II et al.
6,685,742 B1 2/2004 Jackson
6,709,458 B2 3/2004 Michaelson
6,716,247 B2 4/2004 Michaelson
6,723,126 B1 4/2004 Berry
6,730,088 B2 5/2004 Yeh
6,752,832 B2 6/2004 Neumann
6,783,547 B2 * 8/2004 Castro ........................ 623/17.16
6,793,679 B2 9/2004 Michaelson
6,808,538 B2 10/2004 Paponneau
6,814,756 B1 11/2004 Michaelson
6,821,298 B1 11/2004 Jackson
6,835,206 B2 12/2004 Jackson
6,849,093 B2 2/2005 Michaelson
6,866,682 B1 3/2005 An et al.
6,893,464 B2 5/2005 Kiester
6,902,579 B2 6/2005 Harms et al.
6,905,512 B2 6/2005 Paes et al.
6,908,485 B2 6/2005 Crozet et al.
6,953,477 B2 10/2005 Berry
6,955,691 B2 10/2005 Chae et al.
6,962,606 B2 11/2005 Michaelson
6,972,035 B2 12/2005 Michaelson
7,008,453 B1 3/2006 Michaelson
7,022,138 B2 4/2006 Mashburn
7,044,971 B2 5/2006 Suddaby
7,056,343 B2 6/2006 Schafer et al.
7,094,257 B2 8/2006 Mujwid et al.
7,156,874 B2 1/2007 Paponneau et al.
7,311,733 B2 12/2007 Metz-Stavenhagen
7,384,431 B2 6/2008 Berry
7,981,157 B2 * 7/2011 Castleman et al. ........ 623/17.15
8,231,681 B2 * 7/2012 Castleman et al. ........ 623/17.16
8,252,054 B2 * 8/2012 Greenhalgh et al. ....... 623/17.11
8,268,004 B2 * 9/2012 Castleman et al. ........ 623/17.16
8,292,963 B2 * 10/2012 Miller et al. ............... 623/17.16
2002/0082695 A1 6/2002 Neumann
2003/0045877 A1 * 3/2003 Yeh ................................ 606/61
2003/0050701 A1 3/2003 Michaelson
2003/0191531 A1 10/2003 Berry
2003/0199980 A1 10/2003 Siedler
2004/0002762 A1 1/2004 Hawkins
2004/0049271 A1 3/2004 Biedermann et al.
2004/0102848 A1 5/2004 Michaelson
2004/0153160 A1 8/2004 Carrasco
2004/0167626 A1 8/2004 Geremakis et al.
2004/0186569 A1 9/2004 Berry
2004/0249461 A1 12/2004 Ferree
2004/0254643 A1 12/2004 Jackson
2005/0004673 A1 1/2005 Kluger
2005/0010294 A1 1/2005 Michaelson
2005/0015149 A1 1/2005 Michaelson
2005/0021041 A1 1/2005 Michaelson
2005/0085910 A1 4/2005 Sweeney
2005/0096744 A1 5/2005 Trieu
2005/0113916 A1 5/2005 Branch
2005/0113921 A1 5/2005 An et al.
2005/0113924 A1 5/2005 Buttermann
2005/0187634 A1 8/2005 Berry
2005/0209697 A1 9/2005 Paponneau et al.
2006/0004447 A1 1/2006 Mastrorio
2006/0058877 A1 3/2006 Gutlin
2006/0058878 A1 3/2006 Michaelson
2006/0058879 A1 3/2006 Metz-Stavenhagen
2006/0074490 A1 4/2006 Sweeney
2006/0079962 A1 4/2006 Michaelson
2006/0100710 A1 5/2006 Gutlin et al.
2006/0224241 A1 10/2006 Butler et al.
2006/0241762 A1 10/2006 Kraus
2006/0241770 A1 10/2006 Rhoda et al.
2007/0028710 A1 2/2007 Kraus
2007/0100340 A1 5/2007 Lange et al.
2007/0168036 A1 7/2007 Ainsworth et al.
2007/0191954 A1 8/2007 Hansell et al.
2007/0241770 A1 10/2007 Rohe et al.
2007/0250171 A1 10/2007 Bonin
2007/0255407 A1 11/2007 Castleman et al.
2007/0255408 A1 11/2007 Castleman et al.
2007/0255409 A1 11/2007 Dickson et al.
2007/0255410 A1 11/2007 Dickson
2007/0255421 A1 11/2007 Dickson
2008/0004705 A1 1/2008 Rogean et al.
2008/0103601 A1 5/2008 Biro et al.
2008/0147193 A1 6/2008 Matthis et al.
2008/0161926 A1 7/2008 Melkent et al.
2008/0167720 A1 7/2008 Melkent
2008/0177387 A1 7/2008 Parimore et al.
2008/0243254 A1 10/2008 Butler
2008/0281424 A1 11/2008 Parry et al.
2010/0179657 A1 * 7/2010 Greenhalgh et al. ....... 623/17.11
2010/0274357 A1 10/2010 Miller et al.
2011/0172716 A1 * 7/2011 Glerum ......................... 606/279
2011/0224793 A1 * 9/2011 Fortin et al. ................ 623/17.12
2012/0022654 A1 * 1/2012 Farris et al. ................ 623/17.16
2012/0323329 A1 * 12/2012 Jimenez et al. ............ 623/17.16

* cited by examiner

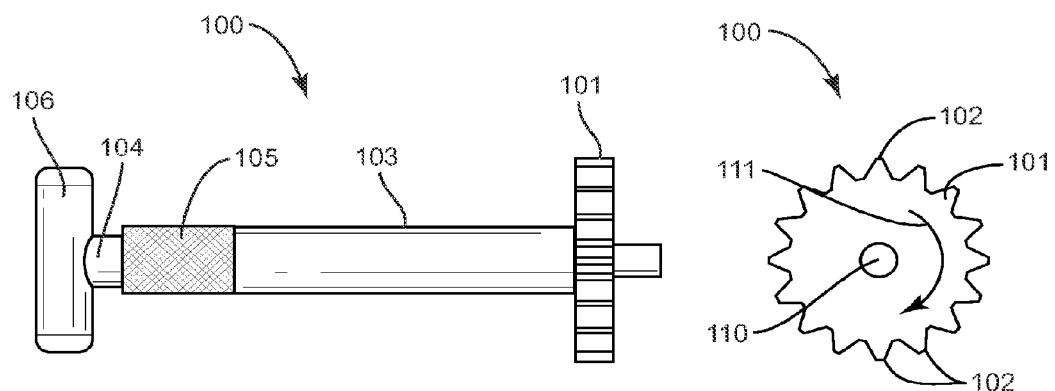
FIG. 12
FIG. 13
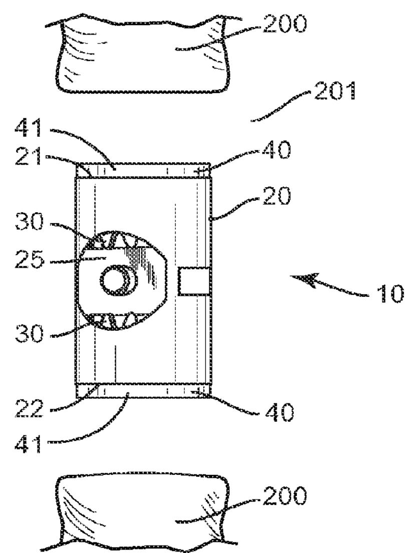
FIG. 14

EXPANDABLE MEDICAL IMPLANT

CROSS-REFERENCE TO RELATED APPLICATION

This application is a divisional of co-pending application Ser. No. 13/015,231, filed on Jan. 27, 2011, which is herein incorporated by reference in its entirety.

BACKGROUND

The present application is directed to a medical implant, and more particularly, to an expandable medical implant with rotating collars that are positioned within a base.

Various medical surgical procedures use an implant that is positioned within the patient between supporting skeletal structures. One example is an implant positioned between vertebral members of the spine. The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

Various conditions may lead to damage of the intervertebral discs and/or the vertebral members. The damage may result from a variety of causes including but not limited to a specific event such as trauma, a degenerative condition, a tumor, or infection. Damage to the intervertebral discs and vertebral members can lead to pain, neurological deficit, and/or loss of motion.

Various procedures include replacing the entirety or a section of a vertebral member, the entirety or a section of an intervertebral disc, or both. One or more replacement implants may be inserted to replace the damaged vertebral members and/or discs. The implants are configured to be inserted into the defect space and contact against the remaining adjacent vertebral members.

The implant may also be used in applications with other skeletal structures. Examples include replacing long bones or portions of appendages such as the legs and arms, or a rib or other bone that is generally longer than it is wide. Examples include, but are not limited to, a femur, tibia, fibula, humerus, radius, ulna, phalanges, clavicle, and ribs.

It may be advantageous for the implants to be adjustable to vary one or more dimensions. The adjustability may ensure that the implants properly accommodate the space between the skeletal structures. The adjustability may also ensure that the implants adequately contact and support the skeletal structures.

SUMMARY

The present application is directed to an expandable medical implant for supporting skeletal structures. The implant may include a base having a first end, a second end, and a sidewall extending between the ends and forming an interior passage extending between the first and second ends. A first collar may be completely positioned within the base at the first end and a second collar may be completely positioned within the base at the second end. Each of the first and second collars may include threaded interiors. The implant may also include a first post that is threaded to the first collar and travels within the first collar and a second post that is threaded to the second collar and travels within the second collar. The first and second posts may include heads that are positionable outward from opposing sides of the base. The first and second posts may include legs that overlap within the interior passage.

The implant may also include a tubular base with a sidewall and a hollow interior space with opposing first and second open ends. The base may include an opening that extends through the sidewall between the first and second ends and may include a longitudinal axis that extends through the first and second ends and the hollow interior space. The implant may include first and second cylindrical collars each with a threaded interior surface and teeth positioned at one end. Each of the collars may be positioned within the hollow interior space of the base with the first collar positioned inward from the first end and the second collar positioned inward from the second end. The first and second collars may be spaced apart along a longitudinal axis of the base. The implant may also include first and second posts each with a head and threaded outwardly extending legs. The head of the first post may be positionable outward from the first end of the base with the legs extending into the first collar with the threaded legs engaging with the threaded interior surface of the first collar, and the head of the second post may be positionable outward from the second end of the base with the legs extending into the second collar with the threaded legs engaging with the threaded interior surface. The legs of the first and second posts may be in an overlapping arrangement along the longitudinal axis of the base.

The application also includes methods of spacing apart skeletal structures. The methods may include positioning an implant while at a first reduced height within a space between skeletal structures. The implant may include first and second elongated posts that are positioned in an overlapping arrangement within a base. The method may include simultaneously rotating first and second collars that are contained within the base with the first collar rotating in a first direction and the second collar rotating in a second direction. The method may also include simultaneously moving the first post that is threaded to the first collar outward away from the base and moving the second post that is threaded to the second collar outward away from the base thereby increasing a height of the implant to a second expanded height.

The various aspects of the various embodiments may be used alone or in any combination, as is desired.

BRIEF DESCRIPTION OF THE DRAWINGS

FIG. 12 is side view of an actuating instrument.

FIG. 13 is an end view of a gear of an actuating instrument.

FIG. 14 is a side view of an implant with a reduced overall height positioned in a space between skeletal structures.

DETAILED DESCRIPTION

Figure 1:
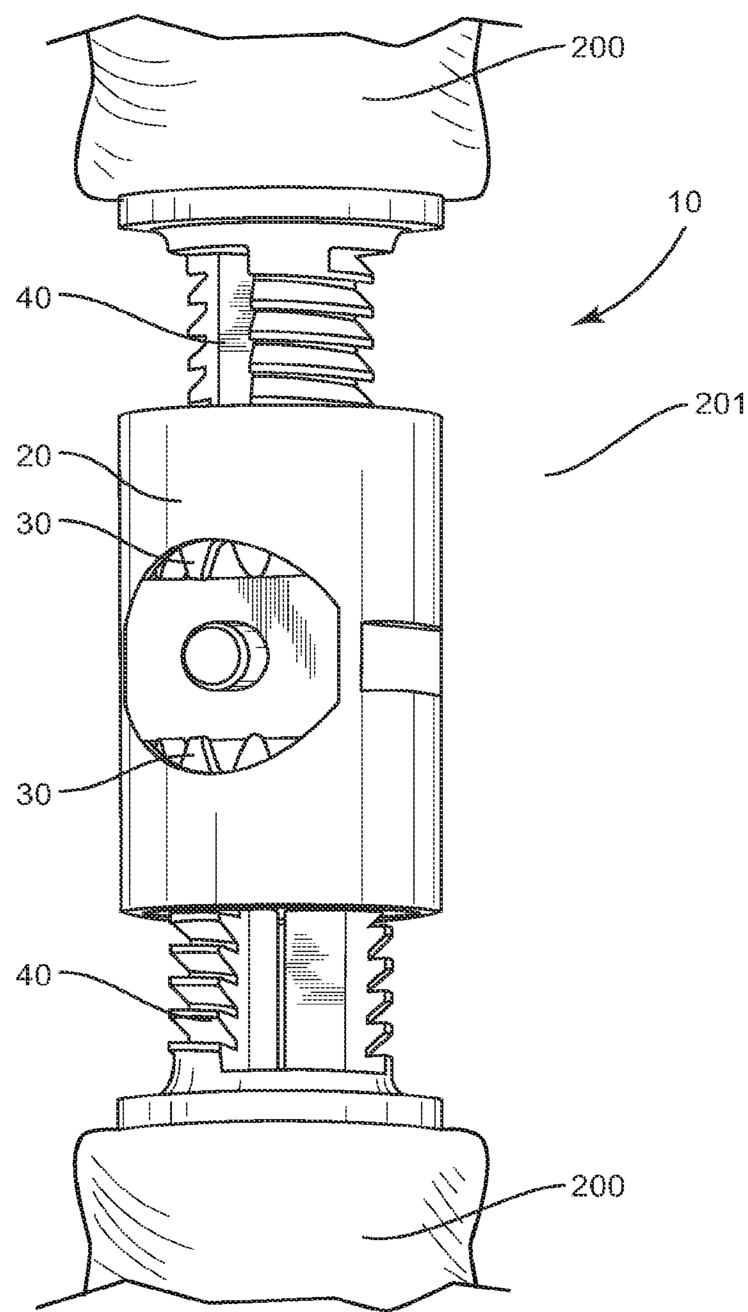
FIG. 1 is a perspective view of an implant positioned between skeletal structures.

The present application is directed to an implant for spacing apart skeletal structures. FIG. 1 illustrates an implant 10 that is positioned within a space 201 formed between skeletal structures 200. The implant 10 includes a base 20 with a hollow interior. Collars 30 are positioned within the hollow interior and are rotatable relative to the base 20. The collars 30 are threaded along an inner surface. Threaded posts 40 extend outward from the base 20 and are threaded into the collars 30. Rotation of the collars 30 adjusts an amount that the threaded posts 40 extend outward from the base 20. An overall height of the implant 10 can be adjusted to accommodate the size of the space 201 and for the posts 40 to contact against and space apart the skeletal structures 200.

Figure 2:
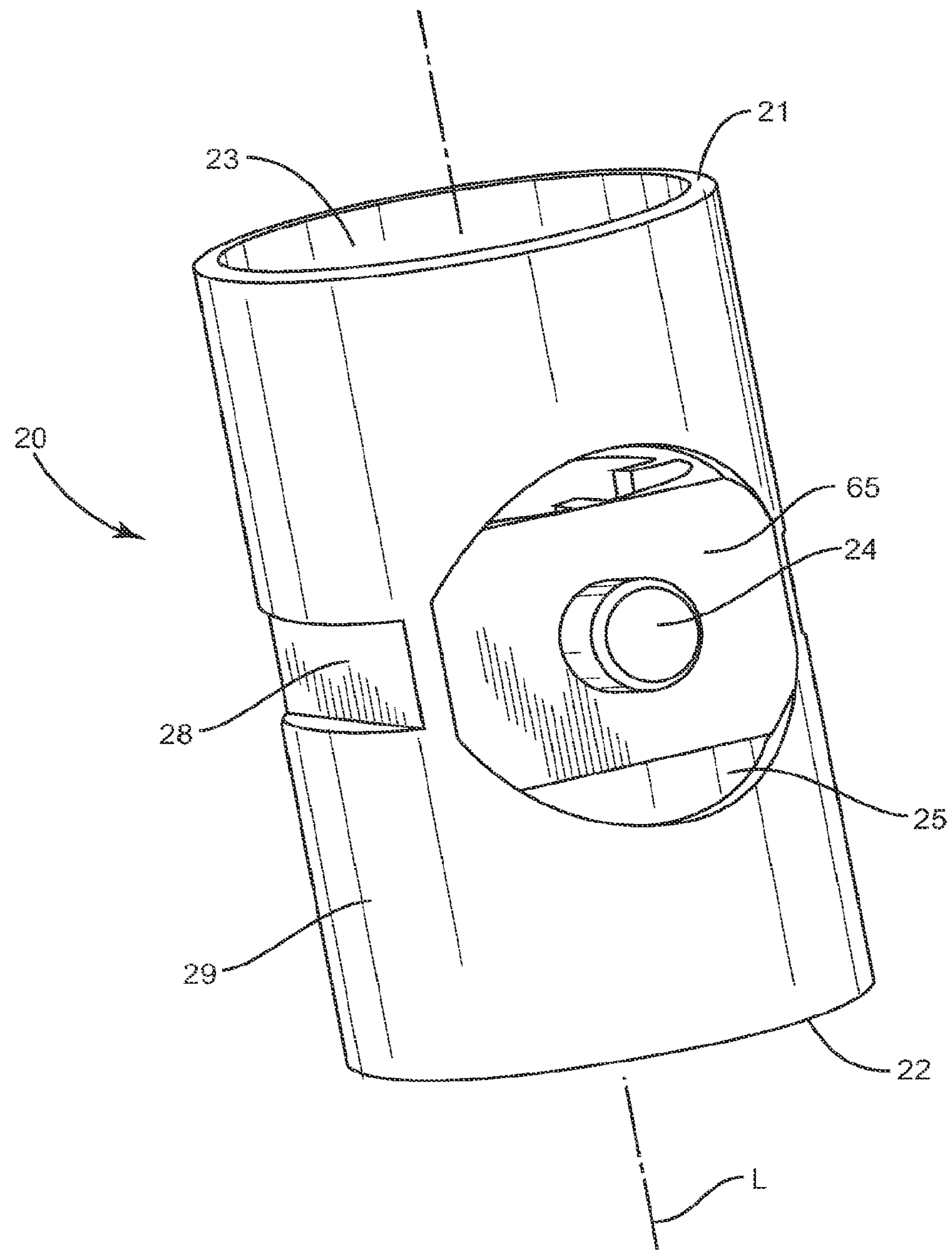
FIG. 2 is a perspective view of a side of a base.
Figure 3:
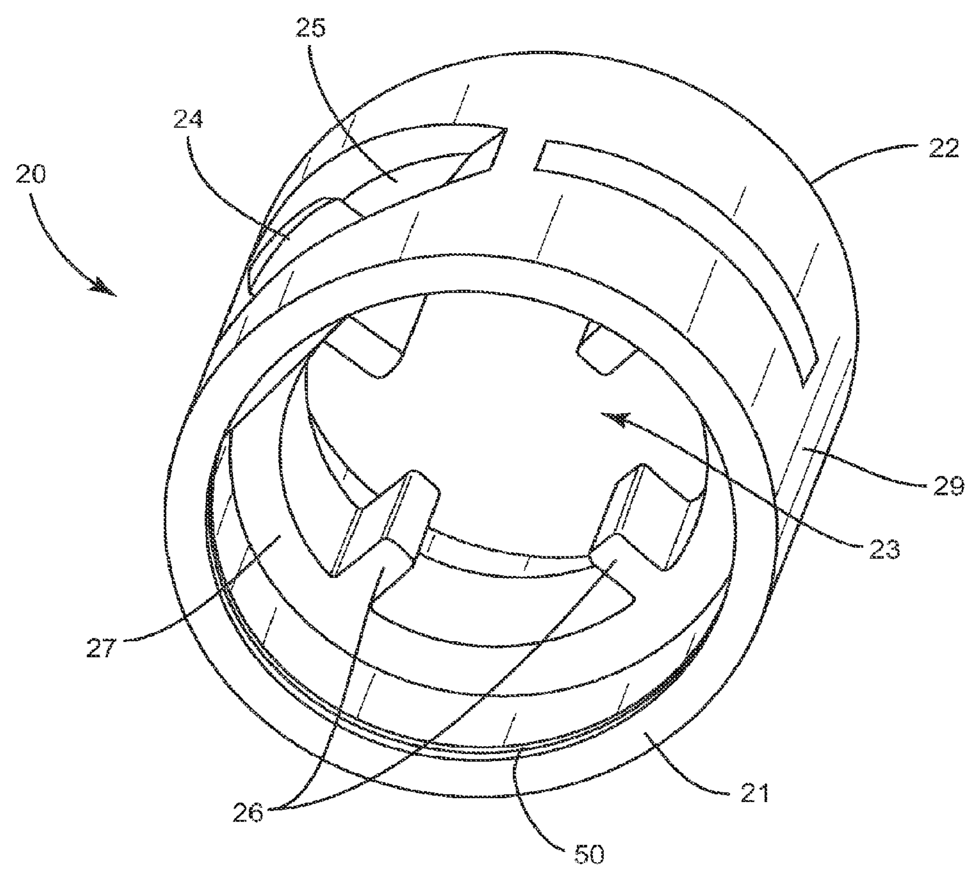
FIG. 3 is a perspective view of the base of FIG. 2 looking into a first end.

The base 20 forms a housing for the collars 30 and the posts 40. FIGS. 2 and 3 illustrate a base 20 that includes a sidewall 29 that extends between a first end 21 and an opposing second end 22. The base 20 includes a longitudinal axis L that extends through each of the ends 21, 22. The base 20 is hollow with an interior space 23 for receiving the collars 30 and posts 40. The base 20 may include a circular cross-sectional shape as best illustrated in FIG. 3. Base 20 may also include various other cross-sectional shapes, including but not limited to rectangular, triangular, oval, and combinations thereof.

The base 20 includes an opening 25 in the sidewall 29. The opening 25 provides access to the collars 30 as will be explained in detail below. FIG. 2 illustrates the opening 25 equally spaced between the first and second ends 21, 22. The opening 25 may also be positioned in closer proximity to one of the ends 21, 22. The base 20 may include a single opening 25 such that the collars 30 are shielded and exposed at just one location in the base 20. Alternatively, the base 20 may include two or more openings 25 for additional access to the interior space 23 and the collars 30 and/or posts 40. The size and shape of the openings 25 may vary depending upon the application. Further, the size of the opening 25 and/or the collars 30 may be such that the collars 30 are completely positioned within the base 20 and not exposed through the opening 25.

A mount 24 is positioned in the opening 25 to engage with and position an actuating instrument 100. The mount 24 may be positioned on a support member 65 that is positioned within the interior space 23 of the base 20. The support member 65 extends across the opening 25 but still allows for access to the collars 30. The mount 24 may be centered within the opening 25 to be equally-distanced from each of the collars 30 that are exposed in the opening 25. The mount 24 may include one or more protrusions and/or one or more openings (not illustrated) that engage with a tool 300. The mounts 24 may include a variety of sizes and shapes.

Shelves 27 may be positioned in the interior space 23 and radially extend inward from the inner surface of the sidewall 29 as illustrated in FIG. 3. A first shelf 27 is positioned in proximity to the first end 21 to position the first collar 30, and a second shelf 27 is positioned in proximity to the second end 22 to position the second collar 30. One or both of the shelves 27 may be aligned at the opening 25 in the base 20 such that the collars 30 are positioned along the longitudinal axis L of the base for the teeth 36 to be exposed in the opening 25 (see FIG. 1). One or both shelves 27 may further be positioned away from the opening 25.

Extensions 26 may also extend radially inward into the interior space 23 from the inner surface of the sidewall 29. The extensions 26 form passageways for the posts 40 as will be explained below. FIG. 3 illustrates four extensions 26 that divide the interior space 23 into quadrants. Various numbers 26 and configurations of extensions 26 may extend into the interior space 23.

Grooves 50 may extend into the sidewall 29 in proximity to each of the ends 21, 22. The grooves 50 extend around the inner perimeter of the base 20 and function to attach and/or position the collars 30 to the base 20 as will be explained below.

The collars 30 are positioned within the interior space 23 to shield the collars 30. The first collar 30 is mounted in proximity to the first end 21, and the second collar 30 is mounted in proximity to the second end 22. The two collars 30 may be the same, or they may include different shapes and/or sizes.

Figure 4A:
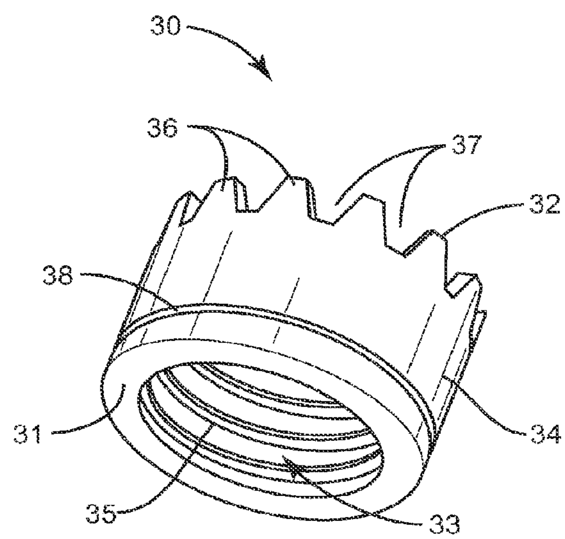
FIG. 4A is an elevated perspective view of a first end of a collar.
Figure 4B:
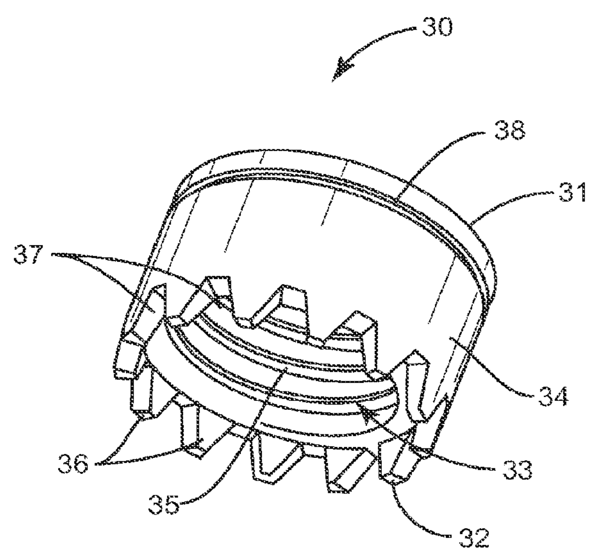
FIG. 4B is an elevated perspective view of a second end of the collar of FIG. 4A.

FIGS. 4A and 4B illustrate views of a collar 30. The collar 30 includes a first end 31 and opposing second end 32 with a sidewall 34 extending between the ends 31, 32. The collar 30 is hollow and includes an interior space 33 that extends between the ends 31, 32. The collar 30 includes a circular cross-sectional shape. The sidewall 34 includes an inner surface with threads 35 that engage with one of the posts 40 as will be explained below. The threads 35 may extend the entirety of the sidewall 34 between the ends 31, 32, or may extend a along a limited distance. Teeth 36 with alternating gaps 37 extend around the second end 32. A groove 38 extends into the exterior surface of the sidewall 34 in proximity to the first end 31.

The collars 30 are positioned within the interior space 23 of the base 20. This positioning protects the collars 30 from contacting against materials within the space 201 that could possible injure the patient, or prevent adjustment of the implant 10. The collars 30 are positioned to be coaxial with the base 20. Further, the collars 30 are mounted at a fixed position along the longitudinal axis L relative to the base 20, and are rotatable relative to the base 20. The collars 30 may be attached in various manners to accomplish these requirements. Each of the two collars 30 may be attached to the base 20 in the same manner, or each may be attached in a different manner.

Figure 5:
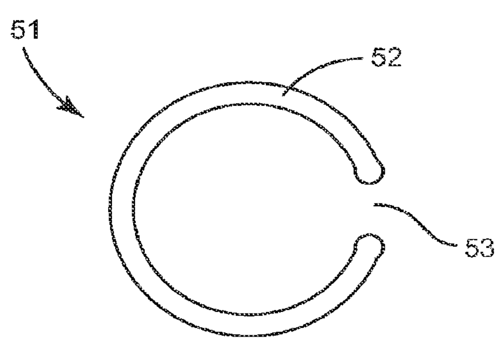
FIG. 5 is a side view of a ring that attaches a base and a collar.

A clip 51 may attach the collar 30 to the base 20. FIG. 5 illustrates a clip 51 with a body 52 having opposing ends separated by a gap 53. The clip 51 is sized to fit around the exterior of the collar 30 and be positioned with the groove 38 that extends around the exterior of the sidewall 34. The clip 51 includes a width to extend outward from the groove 38 and extend into the groove 50 in the interior of the sidewall 29 of the base 20. The clip 51 attaches the collar 30 to the base 20 to prevent the collar 30 from moving along the longitudinal axis L of the base 20, and also allows for the collar 30 to rotate around the longitudinal axis relative to the base 20. Clip 51 may also fit into the groove 50 in the base 20 and provide a floor for the collar 30 to establish an inner positioning location along the longitudinal axis L for the collar 30. In this configuration, the clip 51 does not extend into the groove 38 in the collar 30.

Figure 6:
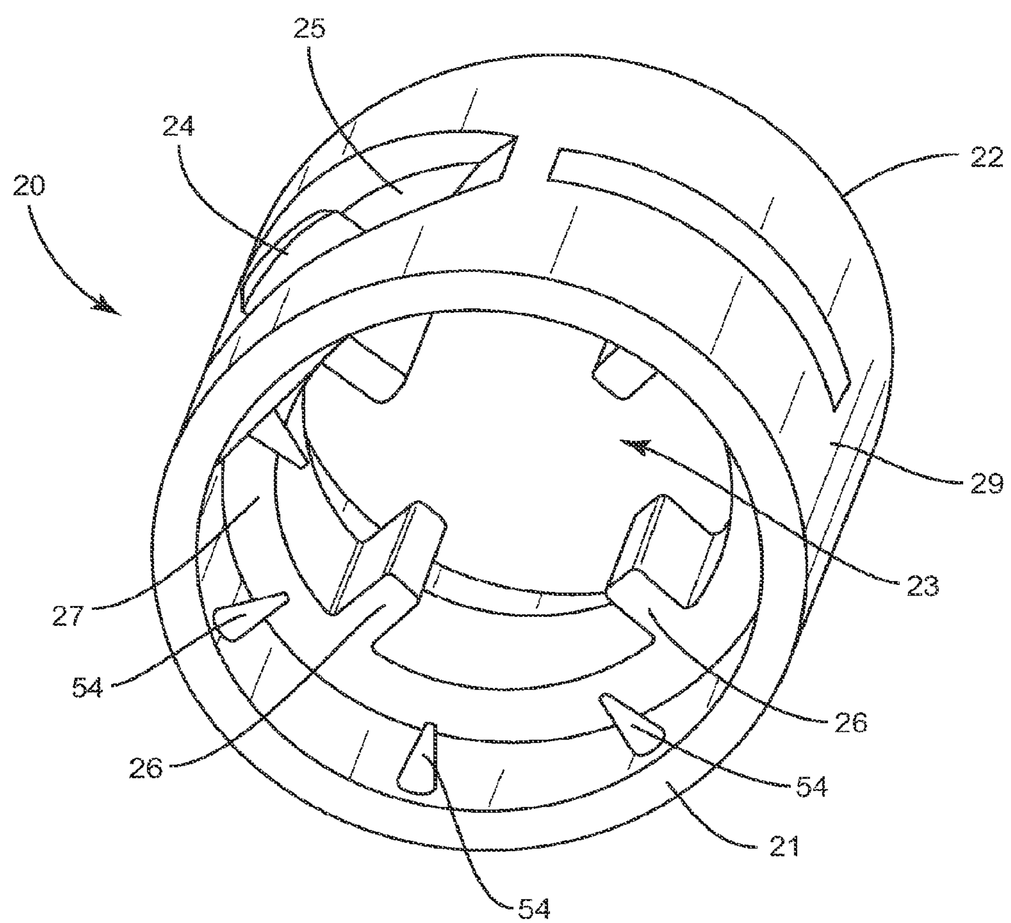
FIG. 6 is a perspective view of a base with pins extending inward into an interior space.

The collar 30 may also be attached to the base 20 by pins 54 that radially extend inward from the base 20. FIG. 6 illustrates pins 54 extending inward into the interior space 23 from the inner surface of the sidewall 29. The pins 54 extend into the groove 38 in the collar 30. This fixes the longitudinal position of the collar 30 relative to the base 20, and allows for the collar 30 to rotate relative to the base 20. The pins 54 may be an integral part of the base 20, or may be separate pieces that are inserted through openings in the sidewall 29. The pins 54 may include various shapes and sizes such as a tapered shape as illustrated in FIG. 6, and a cylindrical shape. The different pins 54 may each be the same size and/or shape, or may include different sizes and/or shapes. The collars 30 may also be attached to the base 20 by other manners, including but not limited to set screws and staking.

Figure 7:
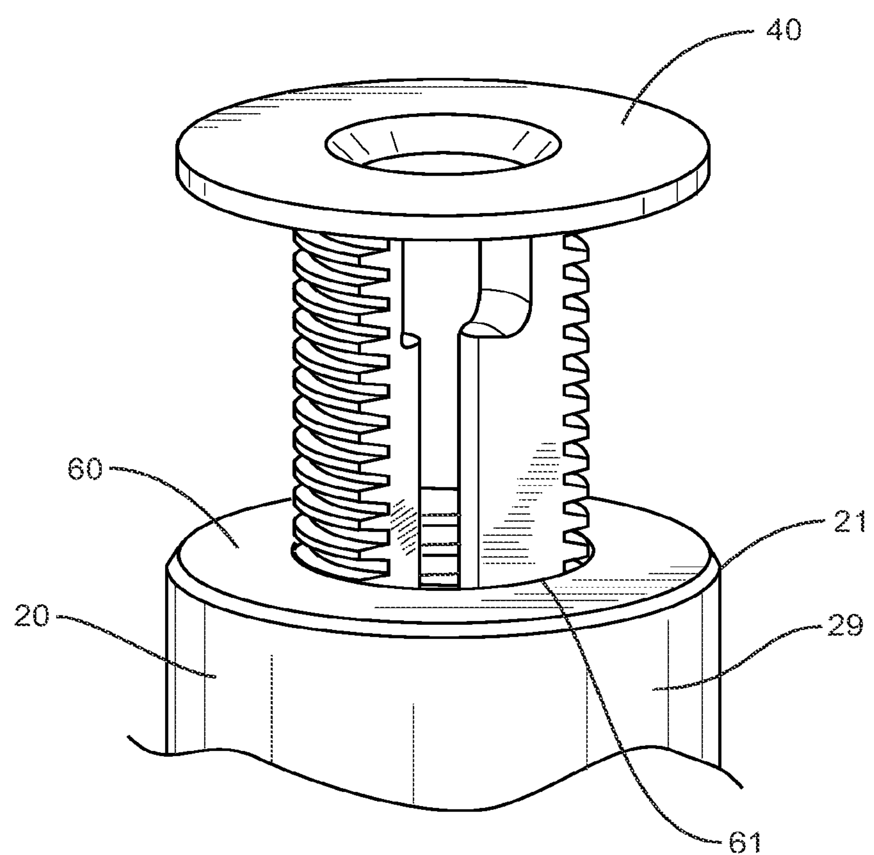
FIG. 7 is a perspective view of a plate attached to base.

One or more plates 60 may be attached to the base 20 to further shield the collars 30. FIG. 7 includes a plate 60 attached at the first end 21 of the base 20 with the understanding that another plate 60 may be attached in a like manner at the second end 22. As illustrated in FIG. 7, the plate 60 captures the collar 30 within the interior space 23 and prevents the collar 30 from escaping from the base 20. When used with a plate 60, the collar 30 may not be attached to the base 20 such as through clips 50 or pins 54 as explained above. Instead, the collar 30 is captured in the interior space 23 of the base 20 and is contained between the plate 60 and the shelf 27 (FIG. 3).

Figure 8:
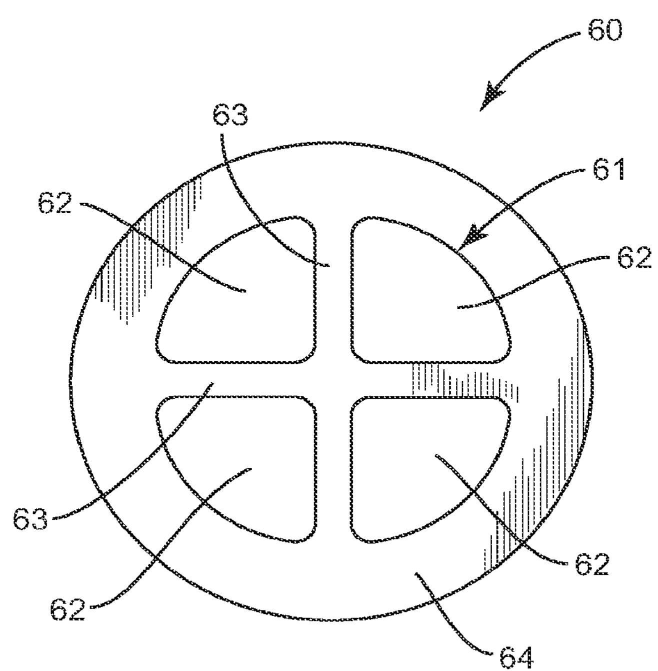
FIG. 8 is a side view of a plate.

FIG. 8 illustrates a plate 60 that includes the opening 61 formed within an outer rim 64. The opening 61 is divided into separate sections 62 by a series of dividers 63. The shapes and sizes and the sections 62 correspond to the posts 40 as will be explained below. Further, the dividers 63 may align with the extensions 26 (FIG. 3) in the base 20 such that the sections 62 align with the openings between the extensions 26 to allow for longitudinal movement of the posts 40. FIG. 8 includes four pie-shaped sections 62. The number, size, and shapes of the sections 62 may vary. In one embodiment, the opening 61 includes a single section 62 without dividers 63. In another embodiment, the number of sections 62 matches the number of legs 42 on the posts 42. In one specific embodiment, a pair of pie-shaped sections 62 are positioned on opposing sides of the plate 60.

Plates 60 are one type of enclosure member for use in containing the collars 30. The enclosure member may also include protrusions that extend inward from the inner surface of the base 20. The protrusions may extend a limited distance into the interior of the base 20.

The posts 40 are adjustable along the longitudinal axis L of the base 20 through the collars 30 to control an overall height of the implant 10. The posts 40 are coupled to the respective collars 30 by threads 48 such that motion of the posts 40 along the longitudinal axis L of the base 20 is induced by rotation of the collars 30. Each of the posts 40 are further constructed to overlap within the base 20 such that the implant 10 can assume a reduced overall height.

Figure 9:
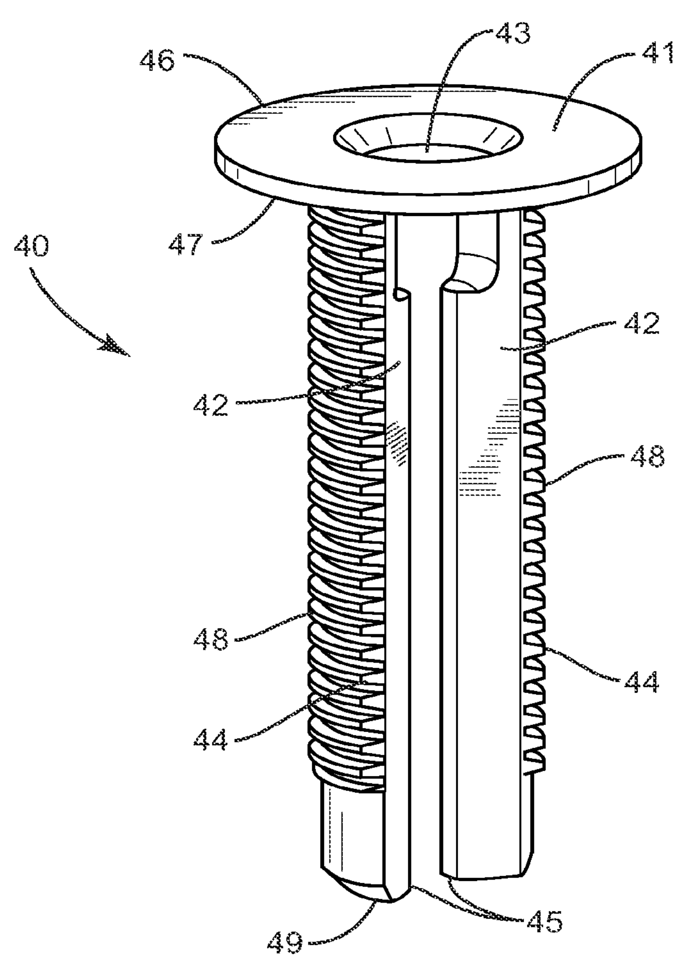
FIG. 9 is a perspective view of a post.
Figure 10:
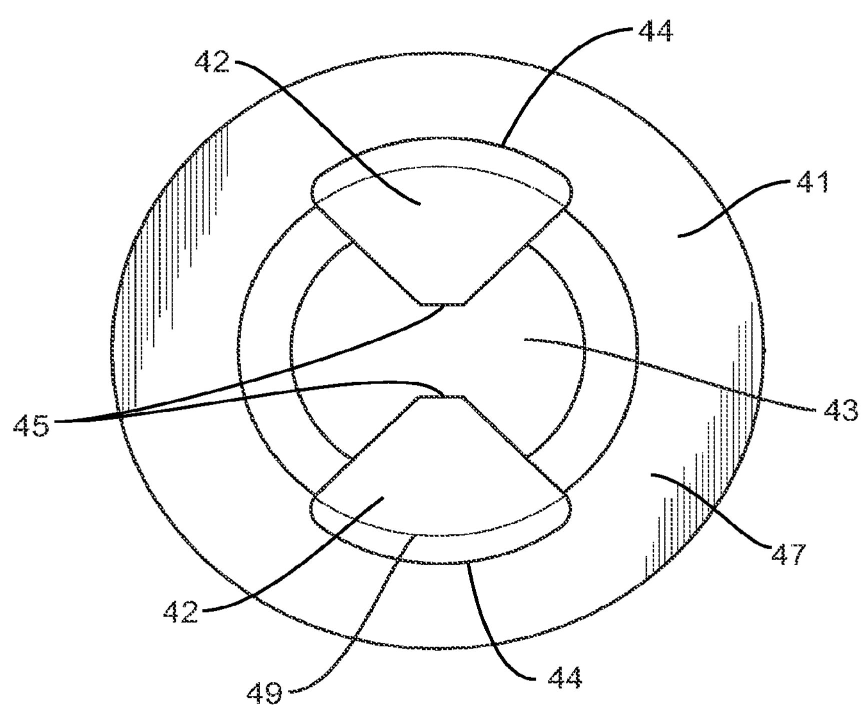
FIG. 10 is an end view of the post of FIG. 9.

FIGS. 9 and 10 illustrate a post 40 that generally includes a head 41 at a first end and outwardly-extending legs 42 that terminate at a distal end 49. The head 41 may include an enlarged size to contact against one of the skeletal structures 201. An opening 43 extends through the head 41 and is in communication with a space formed between the legs 42. FIGS. 9 and 10 include the head 41 having a circular shape, although the head 41 may include various other shapes. The size of the head 41 may further vary depending upon the use. In one embodiment, the size of the head is substantially the same as the base 20. The size of the head 41 may be larger than the base 20 to remain on the exterior of the base 20 when the implant 10 is in a reduced orientation. The head 41 may also be sized relative to the base 20 to fit into the base 20 when the implant 10 is in a reduced orientation.

The head 41 includes an outer face 46 that may include surface features such as teeth and texturing to contact the skeletal structure 201. The outer face 46 may further form a platform for one or more end pieces that attach to the head 41 and contact the skeletal structure 201. In these uses, the outer face 46 may include posts or apertures for attaching to the end piece. In spinal applications, the end pieces may include an angled configuration so the implant 10 will match or alter a lordotic or kyphotic curvature of the spine, or a curvature resulting from scoliosis.

Legs 42 extend outward from an inner face 47 of the head 41. Legs 42 are substantially straight and include an outer lateral side 44 with threads 48, and an opposing inner lateral side 45. The outer lateral sides 44 are curved such that the threads 48 engage with the threads 45 on the inner surface of the collar 30. The inner sides 45 are substantially flat and are spaced apart from one another. As illustrated in FIG. 10, the cross-sectional shape of each of the legs 42 is substantially pie-shaped. In another embodiment, the legs 42 of one posts 40 are connected together with a substantially hour-glass shape with the legs of the other post 40 spaced apart as illustrated in FIGS. 9 and 10 to allow for overlap. Each of the legs 42 may also have a circular cross-sectional shape with one legs 42 having a larger size to extend around and overlap with the opposing legs 42. The posts 40 may include various numbers of legs 42 that extend outward from the head 41.

The cross-sectional shape of the legs 42 corresponds to the shape formed between the extensions 26 in the base 20, and also with the sections 62 formed in the plate 60. The cross-sectional size and shape of the legs 42 may be in close tolerance with the sections 62 and extensions 26. This assists in stabilizing the posts 40 relative to the base 20. This close tolerance may provide one or both of guidance in dynamic operation of the posts 40 and lateral or other structural stability to the posts 40 in the interior space 23 of the base 20.

Figure 11:
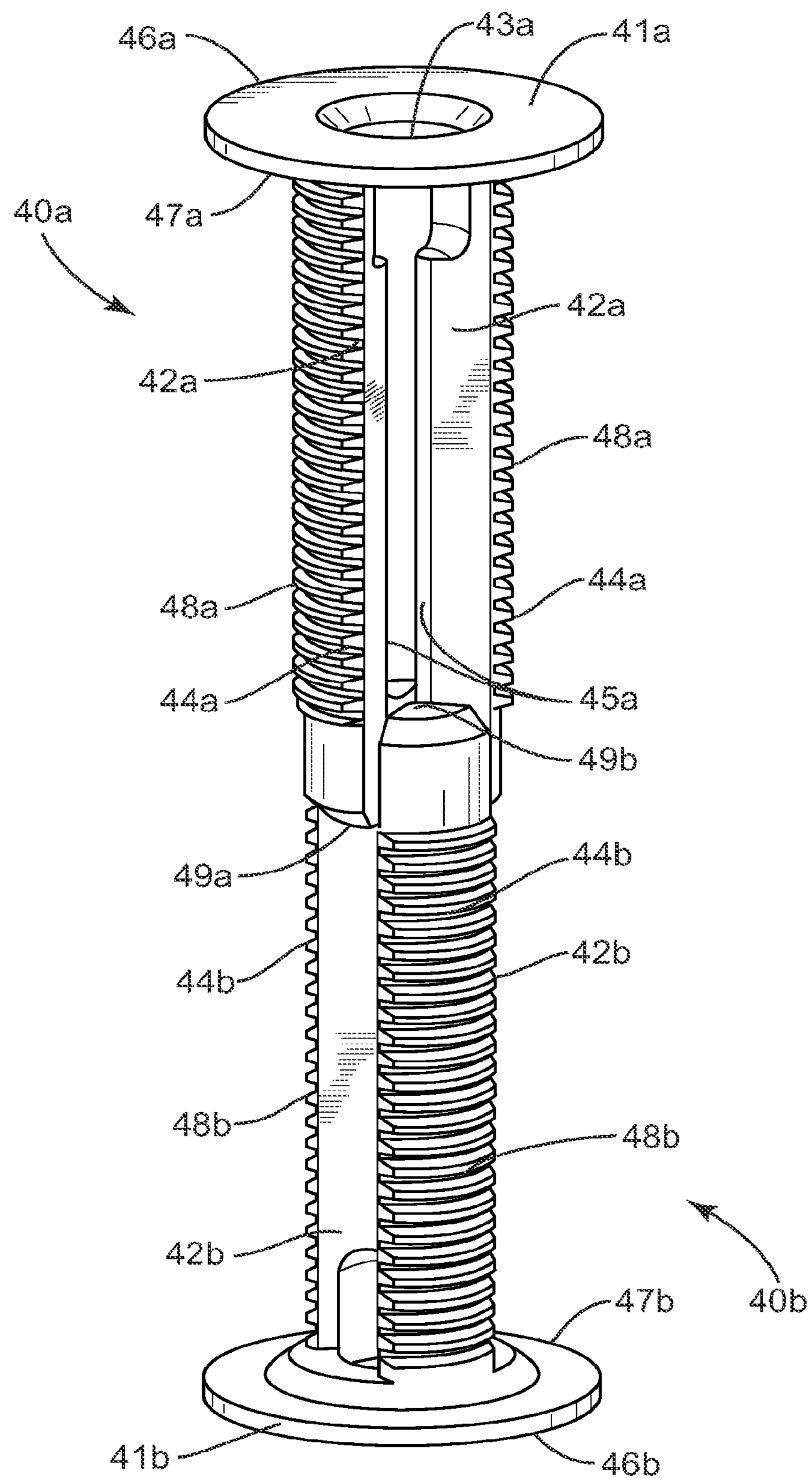
FIG. 11 is perspective view of a pair of posts in an overlapping arrangement.

The shape of the legs 42 also facilitates overlapping movement of the legs 42 with the legs 42 of the opposing posts 40. FIG. 11 illustrates a pair of posts 40 positioned relative to one another (the other elements of the implant have been removed for clarity). For purposes of this Figure, a first one of the posts 40 and its various elements will be identified with the suffix "a", and a second one of the posts 40 and its elements identified with the suffix "b". The pie-shaped legs 42*a*, 42*b* provide for the legs 42*a*, 42*b* to overlap as the posts 40*a*, 40*b* move along the longitudinal axis L of the base 20. The legs 42*a*, 42*b* together form a substantially circular cross-sectional shape in the overlapping arrangement.

FIG. 11 specifically illustrates the distal ends 49*a*, 49*b* of the posts 40*a*, 40*b* being in an overlapping arrangement. The amount of overlap between the posts 40*a*, 40*b* may vary. FIG. 11 illustrates an orientation with a minimal amount of overlap as just a small portion of the legs 42*a* overlap with the opposing legs 42*b*. In one embodiment, this minimal amount of overlap corresponds to a maximum overall height of the implant 10 (i.e., when the posts 42*a*, 42*b* extend a maximum amount outward from the base 20). In one embodiment, the posts 40*a*, 40*b* do not overlap at the maximum overall height with the distal ends 49*a*, 49*b* being spaced apart along the longitudinal axis L. When the implant 10 is at a minimum overall height, the amount of overlap between the legs 42*a*, 42*b* is a greater amount. In one embodiment, the minimum height positions the distal ends 49*a*, 49*b* at or in close proximity to the opposing heads 41*a*, 41*b*.

The term "overlap" and variations of the term used herein refer to components that mesh together, intermingle, or interdigitate along their lengths. Components are considered to be configured to overlap when the components have a shape that will allow portions of the components to pass by one another and occupy a common cross-sectional plane along a length of the components. As applied to the embodiment illustrated in FIG. 11, the first post 40*a* is configured to overlap with the second post 40*b* because the legs 42*a* of the first post 40*a* are shaped to fit in a common cross-sectional plane with legs 42*b* of the second post 40*b* along a length of the first and second posts 40*a*, 40*b*. More particularly for the illustrated embodiment, the first post 40*a* and the second post 40*b* each include two opposing, overlapping legs 42*a* and 42*b*. Each illustrated leg 42*a*, 42*b* is located substantially at a quarter point of a cross-section of the base 20. In other embodiments, there may only be two legs such that each post 40*a*, 40*b* includes a maximum amount of material to the exclusion of separator components, as noted above. Some embodiments of the posts 40*a*, 40*b* may include more than two pairs of overlapping legs 42*a*, 42*b* that distribute the load carried by the posts 40*a*, 40*b* around a periphery of the base to reduce loading eccentricities, and therefore stresses in the materials of the posts. The overlap provides for the overall height of the implant 10 to be smaller in the reduced orientation. In one embodiment, an expanded height with the posts 40 positioned outward is at least twice that of a reduced height.

In one embodiment, the legs 42*a*, 42*b* of each of the posts 40*a*, 40*b* have substantially the same length measured between the head 41*a*, 41*b* and the respective end 49*a*, 49*b*. Alternatively, one of the posts 40*a* or 40*b* includes longer legs 42*a*, 42*b*.

The first and second collars 30 are positioned to be turned simultaneously with an actuating instrument 100. FIGS. 12 and 13 illustrate an actuating instrument 100 to simultaneously turn the collars 30. The actuating instrument 100 includes a single gear 101 with gear teeth 102 configured to engage with the teeth 36 on the collars 30. A distal end of the gear 101 is configured to engage and align with the teeth 36 on the collars 30. FIG. 12 includes the distal end including a protrusion sized to fit within a corresponding opening. FIG. 13 includes an embodiment with the distal end of the gear 101 having an opening 110 sized to receive a corresponding mount 24. The actuating instrument 100 also includes a tube 103 in which a shaft 104 is rotatably coupled. A gripping surface 105 may be applied to an exterior portion of the tube 103. A handle 106 may be included on a proximal end of the shaft 104 for grasping to turn the shaft 104 relative to the tube 103. The shaft 104 is coupled to the gear 101. As shown by arrow 111 in FIG. 13, rotation of the gear 101 results in motion relative to the gear 101 at the top of the gear 101 in a first direction and motion at the bottom of the gear 101 in a second direction opposite from the first direction. This configuration results in counter-rotation of first and second collars 30 and simultaneous movement of posts 40 toward a collapsed or expanded state.

In the illustrated configuration, the first and second collars 30 are turned in opposite directions by the actuating instrument 100. However, the collars 30 have thread patterns configured such that rotating them in opposite directions results in the first and second posts 40 moving together simultaneously and moving apart simultaneously.

Various other combinations of thread patterns and gears may be used to engage the collars 20. For example and without limitation, an actuating instrument 100 may have two intermeshing gears so that collars above and below would be moved in the same, rather than opposite, rotational directions. This configuration could be operable in conjunction with collars 30 that have opposite thread patterns, for example, one with right-hand threads and one with left-hand threads.

FIG. 14 illustrates an implant 10 in a closed orientation with a reduced overall height for positioning within the space 201 between the skeletal structures 200. The height of the implant 10 is less than the height of the space 201 such that one or both of the posts 40 is spaced away from the skeletal structures 200. This reduced overall height facilitates insertion of the implant 10 into the space 201.

FIG. 14 illustrates an arrangement with the heads 41 of the posts 40 positioned against the ends 21, 22 of the base 20. Other embodiments may include a smallest overall height arrangement with one or both heads 41 spaced away from the base 20. The smallest height may also include one or both of the heads 41 positioned within the base 20.

The implant 10 is positioned into the space 201 with the opening 25 accessible for the actuating instrument 100. The surgical personnel insert the distal end of the instrument 100 into the patient and align the gear 300 such that the teeth 102 engage with the teeth 26 on both of the collars 30.

The surgical personnel then rotate the handle 106 causing rotation of the gear 101. The gear 101 is engaged with the teeth 36 of the collars 30 causing the collars 30 to also rotate. This rotation causes the collars 30 positioned within the base 20 to rotate relative to the base 20. The threads 35 on the interior of the collars 30 are engaged with the threads 48 on the posts 40. Therefore, the rotation of the collars 30 causes the posts 40 to move along the longitudinal axis L of the base 20. Rotation of the gear 101 in a first direction causes the posts 40 to move outward away from the base 20 and to increase the overall height of the implant 10 Likewise, rotation in a second direction causes the posts 40 to move inward towards the base 20 and decrease the overall height.

The surgical personnel rotate the gear 101 such that the posts 40 move outward and into contact with the skeletal structures 200. Once at the proper overall height, the actuating instrument is removed with the implant 10 remaining in the space 201 as illustrated in FIG. 1.

The implant 10 may be locked in this overall height to prevent inadvertent movement of the posts 40 relative to the base 20. This may include attaching a set screw or other like fastener through the base and against one or both of the collars 30 or posts 40. This may also include placing a plug over the teeth 36, or a ratchet lock spring.

The collars 30 are positioned within the base 20 and are shielded from contact against tissue or other elements within the patient. This helps to ensure that the collars 30 are able to rotate and to change the overall height of the implant 10.

In some embodiments, the implant 10 may be expandable to an overall height at least two times the height of the implant 10 in an unexpanded state. For example, the implant 10 may be capable of having a first height between the outer faces 46 of the posts 40, and may be capable of expanding to a second height measured between these outer faces 46 that is at least two times the first height.

The legs 42 of the posts 40 may move through the sections 62 of the plate 60 and/or the spaces formed between the extensions 26 of the base 20. These elements 62, 26 contribute towards preventing the threads 48 of the posts 40 from disengaging with the threads 35 of the respective collars 30. Turning forces that create work along the threads may generate resulting forces that tend to push the legs 42 toward the center of the base 20 as forces are applied to the threads. These elements may contact generally opposite sides of the respective legs 42 to counteract the resulting forces and allow the threads 48 of the legs 42 to remain engaged with the threads 35 of the collars 30.

In some embodiments, the implant 10 may also include a bone growth promoting substance. All or a portion of the interior and/or periphery of the implant 10 may be packed with a suitable bone growth promoting substance or therapeutic composition. For example, and without limitation, one or both of an openings 43 in the posts 40 may be filled with a bone growth promoting substance such as an osteogenic material to promote bone growth. Bone growth promoting substances include, without limitation, autograft, allograft, xenograft, demineralized bone, synthetic and natural bone graft substitutes, such as bioceramics and polymers, and osteoinductive factors. A separate carrier to hold materials within the device may also be used. These carriers may include collagen-based carriers, bioceramic materials, such as BIOGLASS®, hydroxyapatite and calcium phosphate compositions. The carrier material may be provided in the form of a sponge, a block, folded sheet, putty, paste, graft material or other suitable form. The osteogenic compositions may include an effective amount of a bone morphogenetic protein (BMP), transforming growth factor .beta.1, insulin-like growth factor, platelet-derived growth factor, fibroblast growth factor, LIM mineralization protein (LMP), and combinations thereof or other therapeutic or infection resistant agents, separately or held within a suitable carrier material. Placement may be accomplished directly or with the aid of an injection or transfer device of any effective type.

The various elements of the implant 10 may be constructed of biocompatible materials of various types. Examples of implant materials include, but are not limited to, non-reinforced polymers, reinforced polymer composites, PEEK and PEEK composites, shape-memory alloys, titanium, titanium alloys, cobalt chrome alloys, stainless steel, ceramics and combinations thereof. Reinforcing materials may include carbon, fiberglass, metal pieces, or any other effective reinforcing material. The implant 10 may include radiographic markers to provide the ability to monitor and determine radiographically or fluoroscopically the location of the implant within the patient. In some embodiments, the implant elements may be constructed of solid sections of bone or other tissues. In other embodiments, the implant elements are constructed of planks of bone that are assembled into a final configuration. The implant may be constructed of planks of bone that are assembled along horizontal or vertical planes through one or more longitudinal axes of the implant. Tissue materials include, but are not limited to, synthetic or natural autograft, allograft or xenograft, and may be resorbable or non-resorbable in nature. Examples of other tissue materials include, but are not limited to, hard tissues, connective tissues, demineralized bone matrix and combinations thereof. Examples of resorbable materials that may be used include, but are not limited to, polylactide, polyglycolide, tyrosine-derived polycarbonate, polyanhydride, polyorthoester, polyphosphazene, calcium phosphate, hydroxyapatite, bioactive glass, and combinations thereof.

Figure 15:
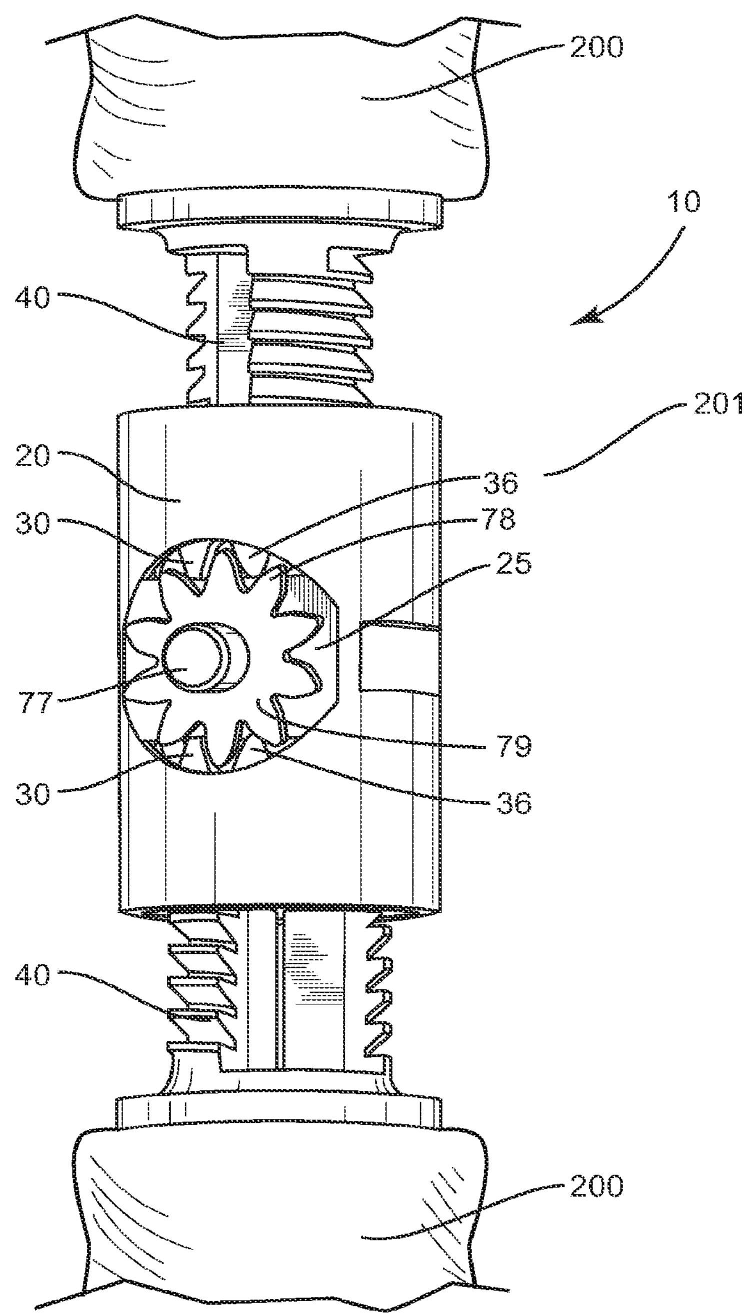
FIG. 15 is a perspective view of an implant positioned between skeletal structures.

FIG. 15 includes an implant 10 with a gear 79 connected to the base 20. The gear 79 is positioned to engage the teeth 36 on the collars 30. The gear 79 includes a mount 77 to receive a tool for applying a rotational force. The mount 77 may be a protrusion as illustrated in FIG. 15, or may include a receptacle. FIG. 15 includes the teeth 36 of the collars 30 be exposed within the opening 25 of the base 20. Teeth 36 may also be recessed in the base 20 and not visible within the opening 25. In the various configurations, the gear 79 is sized and configured to engage with the collars 30 and provide rotation.

The implant 10 may be used at various locations within the body between supporting structural members 200. One example is within the space between vertebral members. Other examples include but are not limited to long bones or portions of appendages such as the legs and arms, or a rib or other bone that is generally longer than it is wide. Examples include, but are not limited to, a femur, tibia, fibula, humerus, radius, ulna, phalanges, clavicle, and ribs.

An extendable implant with a base, collars, and posts is disclosed in U.S. patent application Ser. No. 12/428,988 (now U.S. Patent Application Publication 2010/0274357) filed on Apr. 23, 2009 and herein incorporated by reference in its entirety.

The implant 10 may be used during surgical procedures on living patients. The implant 10 may also be used in a non-living situation, such as within a cadaver, model, and the like. The non-living situation may be for one or more of testing, training, and demonstration purposes.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A method of spacing apart skeletal structures comprising:

positioning an implant while at a first reduced height within a space between skeletal structures, the implant including first and second elongated posts that are positioned in an overlapping arrangement within a base;

simultaneously rotating first and second collars that are contained within the base with the first collar rotating in a first direction and the second collar rotating in a second direction; and simultaneously moving the first post that is threaded to the first collar outward away from the base and moving the second post that is threaded to the second collar outward away from the base thereby increasing a height of the implant to a second expanded height, wherein the base includes opposing first and second open ends the first collar being positioned inward from the first end and the second collar being positioned inward from the second end;

wherein the base includes an opening that extends through a sidewall of the base; and the only access into an interior space of the base is through one of first and second ends and the opening.

2. The method of claim 1, further comprising engaging teeth on the first and second collars that are positioned within an interior of the base and rotating the first and second collars.

3. The method of claim 1, further comprising rotating the first collar and maintaining the first collar within a first longitudinal half of the base and rotating the second collar and maintaining the second collar within an opposing second longitudinal half of the base.

4. The method of claim 1, further comprising maintaining the first collar between a first end of the base and a first shelf on an interior surface of the base and maintaining the second collar between a second end of the base and a second shelf on the interior surface of the base, the first and second shelves being spaced apart along a longitudinal axis of the base.

5. The method of claim 1, wherein the second expanded height is at least twice that of the first reduced height.

6. The method of claim 1, further comprising maintaining the posts in an overlapping arrangement in the second expanded height.

7. The method of claim 1, wherein inner surfaces of the collars include threads that engage threads on outer surfaces of the posts.

8. The method of claim 1, wherein:

the first collar includes teeth that face teeth on the second collar, the teeth on the first collar being apart from the teeth on the second collar; and rotating the first and second collars includes rotating a gear positioned between the first and second collars that simultaneously engages the teeth of the first collar and the teeth of the second collar.

9. The method of claim 8, wherein the gear includes a mount to receive a tool for applying a rotational force.

10. The method of claim 1, wherein:

an inner surface of the base includes at least two spaced apart grooves;

outer surfaces of the first and second collars each include at least one groove;

a first clip is positioned in the groove in the first collar and one of the grooves in the base to attach the first collar with the base; and a second clip is positioned in the groove in the second collar and one of the grooves in the base to attach the second collar with the base.

11. The method of claim 10, wherein the first and second clips each include a body having opposing ends separated by a gap.

12. A method of spacing apart skeletal structures comprising;

providing an expandable medical implant comprising:

a base having a first end, a second end, and a sidewall extending between the ends and forming an interior passage extending between the first and second ends, a first collar completely positioned within the base at the first end and a second collar completely positioned within the base at the second end, each of the first and second collars including threaded interiors, a first post that is threaded to the first collar and travels within the first collar and a second post that is threaded to the second collar and travels within the second collar, the first and second posts including heads that are positionable outward from opposing sides of the base, the first and second posts each including legs;

positioning the implant while at a first reduced height within a space between skeletal structures;

simultaneously rotating the first and second collars with the first collar rotating in a first direction and the second collar rotating in a second direction; and simultaneously moving the first post outward away from the base and moving the second post outward away from the base thereby increasing a height of the implant to a second expanded height;

wherein the first and second ends of the base each include an aperture in communication with the interior passage;

wherein the base includes an opening that extends through a sidewall of the base; and wherein the only access into the interior space of the base is through one of the apertures and the opening.

13. The method of claim 12, wherein the legs overlap within the interior passage.

14. The method of claim 12, wherein the legs interdigitate within the interior passage.

15. The method of claim 12, wherein:

the first collar includes teeth that face teeth on the second collar, the teeth on the first collar being apart from the teeth on the second collar; and rotating the first and second collars includes rotating a gear positioned between the first and second collars that simultaneously engages the teeth of the first collar and the teeth of the second collar.

16. The method of claim 15, wherein the gear includes a mount to receive a tool for applying a rotational force.

17. A method of spacing apart skeletal structures comprising:

providing an expandable medical implant comprising:

a tubular base with a sidewall and a hollow interior space with opposing first and second open ends, the base including an opening that extends through the sidewall between the first and second ends, the base including a longitudinal axis that extends through the first and second ends and the hollow interior space, wherein the only access into the interior space of the base is through one of the first and second ends and the opening, first and second cylindrical collars each with a threaded interior surface and teeth positioned at one end, each of the collars positioned within the hollow interior space of the base with the first collar positioned inward from the first end and the second collar positioned inward from the second end, the first and second collars being spaced apart along a longitudinal axis of the base, and first and second posts each with a head and threaded outwardly extending legs, the head of the first post positionable outward from the first end of the base with the legs extending into the first collar with the threaded legs engaging with the threaded interior surface of the first collar, and the head of the second post positionable outward from the second end of the base with the legs extending into the second collar with the threaded legs engaging with the threaded interior surface, the legs of the first and second posts being in an overlapping arrangement along the longitudinal axis of the base;

positioning the implant while at a first reduced height within a space between skeletal structures;

simultaneously rotating the first and second collars with the first collar rotating in a first direction and the second collar rotating in a second direction; and simultaneously moving the first post outward away from the base and moving the second post outward away from the base thereby increasing a height of the implant to a second expanded height.

* * * * *